United States Patent
Liu et al.

(10) Patent No.: US 9,849,183 B2
(45) Date of Patent: Dec. 26, 2017

(54) COMPOUND PRESCRIPTION COLLOIDAL EYEDROP GEL AND METHODS OF MAKING THE SAME

(71) Applicant: NATIONAL CHIAO TUNG UNIVERSITY, Hsinchu (TW)

(72) Inventors: Dean-Mo Liu, Hsinchu County (TW); Yi-Ling Wang, Kaohsiung (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 15/063,523

(22) Filed: Mar. 8, 2016

(65) Prior Publication Data

US 2017/0189535 A1    Jul. 6, 2017

(30) Foreign Application Priority Data

Jan. 5, 2016   (TW) .............................. 105100196 A

(51) Int. Cl.

| | | |
|---|---|---|
| A61K 47/36 | (2006.01) | |
| A61K 9/00 | (2006.01) | |
| A61K 9/10 | (2006.01) | |
| A61K 31/382 | (2006.01) | |
| A61K 31/5575 | (2006.01) | |
| A61K 9/06 | (2006.01) | |
| A61K 45/06 | (2006.01) | |
| A61K 9/107 | (2006.01) | |

(52) U.S. Cl.
CPC ............ *A61K 47/36* (2013.01); *A61K 9/0048* (2013.01); *A61K 9/06* (2013.01); *A61K 9/1075* (2013.01); *A61K 31/382* (2013.01); *A61K 31/5575* (2013.01); *A61K 45/06* (2013.01)

(58) Field of Classification Search
CPC ............ A61K 2300/00; A61K 31/192; A61K 31/198; A61K 31/282; A61K 31/337; A61K 31/4375; A61K 31/4545; A61K 31/513; A61K 31/675; A61K 31/69; A61K 31/704; A61K 31/7068; A61K 33/24; A61K 39/39533; A61K 45/06; A61K 41/0038; A61K 31/382; A61K 31/5575; A61K 47/36; A61K 9/0048; A61K 9/1075; A61K 9/06
See application file for complete search history.

(56) References Cited

U.S. PATENT DOCUMENTS

| | | |
|---|---|---|
| 2012/0022505 A1 | 1/2012 | Dacquay et al. |
| 2012/0282328 A1 | 11/2012 | Cipolla et al. |
| 2013/0202551 A1 | 8/2013 | Satake et al. |
| 2013/0230495 A1* | 9/2013 | Chiou .................... A61K 47/36 424/93.7 |
| 2014/0025022 A1 | 1/2014 | Cadden et al. |
| 2015/0250891 A1 | 9/2015 | Venkatraman et al. |
| 2015/0297731 A1* | 10/2015 | Chiou ................. A61K 9/0051 514/236.2 |

FOREIGN PATENT DOCUMENTS

| | | |
|---|---|---|
| CN | 102115515 A | 7/2011 |
| CN | 102028694 B | 3/2012 |
| CN | 102470115 B | 4/2014 |
| JP | 2011111441 A | 6/2011 |
| JP | 2011132227 A | 7/2011 |
| JP | 2012031075 A | 2/2012 |
| KR | 20040097804 A | 11/2004 |
| TW | 201249462 A | 12/2012 |
| TW | 201536350 A | 10/2015 |
| WO | 9522315 | 8/1995 |

OTHER PUBLICATIONS

Shefali et al (Carbohydrate Polymer, 2014, vol. 102, pp. 117-124).*
Hsiao et al (Acta Biomaterialia, online date of Mar. 2014, vol. 10, pp. 3188-3196).*
Ging-Ho Hsiue et al., "Preparation of controlled release ophthalmic drops, for glaucoma therapy using thermosensitive poly-N-isopropylacrylamide", Biomaterials, 2002, 23(2), 457-462.
Shefali Katiyar et al., "In situ gelling dorzolamide loaded chitosan nanoparticles for the treatment of glaucoma", Carbohydrate Polymer, 102(2014), 117-124.
Paul Harasymowycz et al., "Latanoprost versus timolol gel-forming solution once daily in primary open-angle glaucoma or ocular hypertension", Can J Ophthalmol., vol. 42., No. 1., pp. 75-81., 2007.
Viviana P. Costa et al., "Anti-glaucoma drug-loaded contact lenses prepared using supercritical solvent impregnation", The Journal of Supercritical Fluids, 53(2010), 165-173.
Meng-Hsuan Hsiao et al., "A temperature-induced and shear-reversible assembly of latanoprost-loaded amphiphilic chitosan colloids: Characterization and in vivo glaucoma treatment", Acta Biomaterialia 10 (2014) 3188-3196.

* cited by examiner

*Primary Examiner* — Mark V Stevens
(74) *Attorney, Agent, or Firm* — CKC & Partners Co., Ltd.

(57) ABSTRACT

The present disclosure herein provides a compound prescription colloidal eyedrop gel. The compound prescription colloidal eyedrop gel includes a plurality of carboxymethyl-hexanoyl chitosan (CHC) micelles, a basic structural stabilizer connecting the plurality of CHC micelles, a first drug inside the CHC micelle, and a second drug outside the CHC micelle.

11 Claims, 6 Drawing Sheets

COMPOUND PRESCRIPTION COLLOIDAL EYEDROP GEL AND METHODS OF MAKING THE SAME

RELATED APPLICATIONS

This application claims priority to Taiwan Application Serial Number 105100196, filed Jan. 5, 2016, which is herein incorporated by reference.

BACKGROUND

Field of Disclosure

The present disclosure relates to a prescription colloidal gel. More particularly, the present disclosure relates to a compound prescription colloidal eyedrop gel.

Description of Related Art

Glaucoma is the second most blindness-causing disease worldwide, and the main cause is the high ocular pressure. The present methods of treating glaucoma are primarily conventional surgeries, laser surgeries, or the medication.

Conventional surgeries perform treatments through operations. Despite immediate effect of treatment, conventional surgeries suffer from rather high surgery risks, possibilities of complications such as bacterial infections, inflammations, or concurrent cataract, while patients usually need to pay higher expenses. Laser surgeries have advantages of high speed and simplicity over conventional surgeries, but show no instant treating effects and apply only to certain types of glaucoma. Moreover, medication is still required to couple with laser surgeries after the operation, which also brings about the issues of easily-resulted complications and costly expenses. Medication is relatively less expensive and with less complications compared to the two abovementioned kinds of surgeries, shows instant and non-invasive treating effect, and thus is viewed as the first-line treatment that is prioritized over surgical treatments.

The most common prescription form of conventional medication for glaucoma is the eyedrop. However, since the harm caused by glaucoma to optical nerves is permanent and unrecoverable, if the patient chooses the eyedrop medication, the person would have to rely on the eyedrop medication for a lifetime. Meanwhile, the problem of great loss of drugs usually occurs during the process of dropping eyedrops, which reduces the amount of drugs entering into the circulations or target areas, decreases the bioavailability and affects the effect of drugs. Hence, patients need to drop eyedrops frequently, with the dropping frequency of 2-4 times a day to effectively lower the ocular pressure, while frequent negligence of dropping can aggravate the disease and even cause blindness. Accordingly, if the dropping times and frequency can be declined, the life quality of patients can be improved.

Apart from the conventional eyedrop medication, injectable gel can also be applied in the treatment of glaucoma. Through injecting the gel encapsulating the glaucoma drugs into the ocular tissues, glaucoma drugs can be released on a long term while reducing the drug loss. Nevertheless, the general injectable gel ordinarily contains only single prescription, and the process of injection is still invasive. Besides the pain and discomfort before and after the injection, potential inflammations can arise in the wound caused by the injection, accordingly lowering the willingness, frequency, and efficacy of the injection.

On account of this, there is a need for a compound prescription colloidal eyedrop gel to fix the aforementioned problems, with the advantage of longer sustaining period of drugs, slow release of drugs, high bioavailability, and low dropping frequency.

SUMMARY

The present disclosure provides a compound prescription colloidal eyedrop gel. The compound prescription colloidal eyedrop gel includes a plurality of carboxymethyl-hexanoyl chitosan (CHC) micelles, a basic structural stabilizer connecting the plurality of CHC micelles, a first drug inside the CHC micelle, and a second drug outside the CHC micelle. This enables the first drug and the second drug to have different release rates. After one of the drugs is rapidly released, the other one of the drugs can be slowly released to compensate for the insufficiency of the amount of drug release to achieve the effect of constant treatment, with the advantages of the long retention time, the high bioavailability, and the low dropping frequency.

According to an embodiment of the present disclosure, one of the first drug and the second drug is a water-soluble drug, while the other is a lipid-soluble drug.

According to an embodiment of the present disclosure, both the first drug and the second drug are water-soluble or lipid-soluble.

According to an embodiment of the present disclosure, the first drug and the second drug are selected from the group consisting of carbonic anhydrase inhibitors, prostaglandin analogues and beta blockers, and the first drug is different from the second drug.

According to an embodiment of the present disclosure, both the first drug and the second drug have concentrations of about 0.01-50 mg/ml in the compound prescription colloidal eyedrop gel.

According to an embodiment of the present disclosure, the plurality of CHC micelles has a concentration of about 0.1-5% (w/v) in the compound prescription colloidal eyedrop gel.

According to an embodiment of the present disclosure, the compound prescription colloidal eyedrop gel further includes a solvent, and the solvent is water, or both water and an organic solvent, the organic solvent is glycerol, DMSO, ethanol, glycol or a combination thereof, and the solvent has a concentration of about 0.001-20% (w/v) relative to the compound prescription colloidal eyedrop gel.

According to an embodiment of the present disclosure, the compound prescription colloidal eyedrop gel further includes a preservative, and the preservative is benzalkonium chloride (BAK), chlorobutanol, phenylmercuric nitrate or a combination thereof, and the preservative has a concentration of about 0.001-0.01% (w/v) relative to the compound prescription colloidal eyedrop gel.

According to an embodiment of the present disclosure, the basic structural stabilizer is genipin, sodium β-glycerophosphate, sodium hydroxide, alginate or a combination thereof, and the basic structural stabilizer has a concentration of about 0.1-10% (w/v) in the compound prescription colloidal eyedrop gel.

The present disclosure also provides a method of making a compound prescription colloidal eyedrop gel. The method includes providing a first solution comprising a first drug, forming a carboxymethyl-hexanoyl chitosan (CHC) micelle in the first solution and the CHC micelle encapsulates the first drug, adding a second drug to the first solution containing the CHC micelle to form a second solution, adding a basic structural stabilizer to the second solution, and placing the second solution containing the basic structural stabilizer in an environment with a temperature of 30-40° C. to form a compound prescription colloidal eyedrop gel.

According to an embodiment of the present disclosure, forming the carboxymethyl-hexanoyl chitosan (CHC) micelle in the first solution includes adding amphipathic carboxymethyl-hexanoyl chitosan (CHC) powder to the first solution.

According to an embodiment of the present disclosure, the method further includes adding a solvent and a preservative to the second solution before adding the basic structural stabilizer to the second solution.

According to an embodiment of the present disclosure, the method further includes adjusting a pH value of the second solution containing the basic structural stabilizer to 6-8 after adding the basic structural stabilizer to the second solution.

BRIEF DESCRIPTION OF THE DRAWINGS

The features, advantages, and embodiments of the present disclosure can be more fully understood by reading the following detailed description of the embodiment, with reference made to the accompanying drawings as follows.

DETAILED DESCRIPTION

To comprehensively illustrate the content of the present disclosure in details, references will now be made to embodiments of the present disclosure, examples of which are illustrated in the accompanying drawings. These are, however, not the only forms to implement or utilize the present disclosure. The examples or embodiments can be combined or substituted under preferable circumstances, and one example or embodiment can be affiliated to other examples or embodiments without further illustration or explanation. In the following descriptions, many specific details are elaborated for readers to fully comprehend the following embodiments. Nonetheless, the present disclosure can also be carried out under the conditions without the specific details.

As aforementioned, the medication of glaucoma primarily includes the two prescription forms of the eyedrops and the injectable gels. However, eyedrops exhibit defects of the high dropping frequency, the high drug loss rate, and the low bioavailability. Meanwhile, injectable gels not only provide generally only single prescription, but provide the invasive process of injection, which is apt to cause discomfort of patients and problems of infections.

To solve the abovementioned problems, the present disclosure provides a compound prescription colloidal eyedrop gel, which includes a plurality of carboxymethyl-hexanoyl chitosan (CHC) micelles, a basic structural stabilizer connecting the plurality of CHC micelles, first drugs and distinct second drugs. In some embodiments, the compound prescription colloidal eyedrop gel further includes a solvent and a preservative to increase the solubility of the drugs or CHC micelles in the colloidal gel, and enhance the stability of the drugs.

Figure 1:
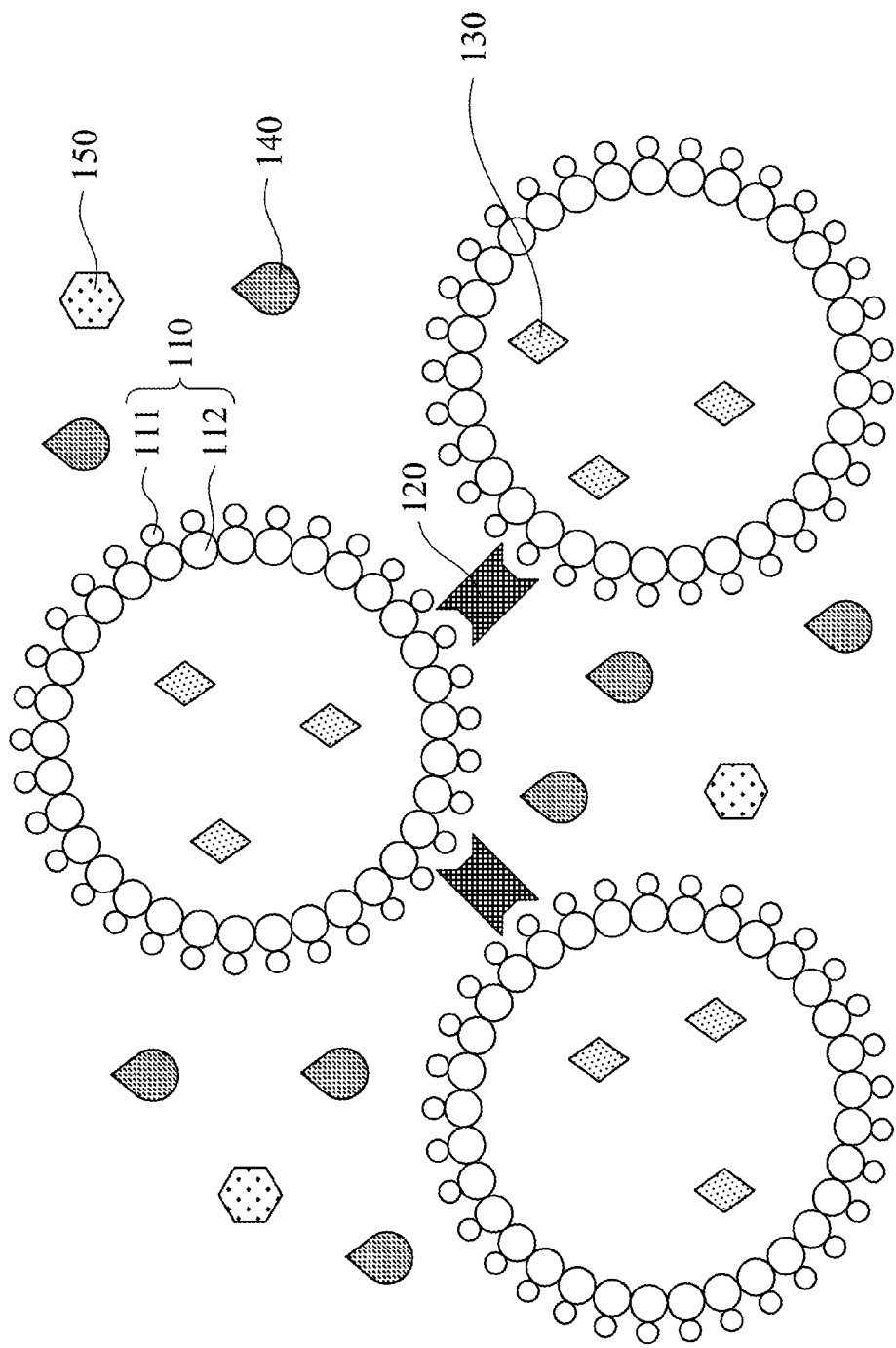
FIG. 1 illustrates a cross-sectional view of a compound prescription colloidal eyedrop gel in accordance with some embodiments of the present disclosure.

Referring to FIG. 1, which illustrates a cross section view of the compound prescription colloidal eyedrop gel in accordance with some embodiments of the present disclosure. As shown in FIG. 1, the compound prescription colloidal eyedrop gel 10 includes a plurality of carboxymethyl-hexanoyl chitosan (CHC) micelles 110, a basic structural stabilizer 120 connecting the plurality of CHC micelles 110, a first drug 130, a second drug 140, a preservative 150, and a solvent (unillustrated). The first drug 130 is inside the CHC micelle 110, while the second drug 140 is outside the CHC micelle 110.

In some embodiments, the plurality of CHC micelles 110 are formed by self-assembly of amphiphilic CHC molecules, while the amphiphilic CHC molecules are formed by the hydrophilic modification and the hydrophobic modification of CHC molecules. In detail, the formation of amphiphilic CHC molecules lies in performing hydrophilic modifications and then hydrophobic modification of the de-acetylated 95% CHC powder with the molecular weight of 50 kDa-250 kDa.

In some embodiments, the hydrophilic modification of the CHC utilizes haloacetic acids, such as the monochloroacetic acid, dichloroacetic acid, trichloroacetic acid, monobromoacetic acid, dibromoacetic acid, or bromochloroacetic acid. In some embodiments, the hydrophobic modification of the CHC utilizes anhydrides, such as acetic anhydride or hexanoic anhydride. The modified CHC has a hydrophilic end and a hydrophobic end at the same time, and thus would gather and self-assemble into the CHC micelles 110 in a solution, and the CHC micelles 110 are biodegradable. In some embodiments, the CHC micelle 110 has a concentration of about 0.1-5% (w/v) in the compound prescription colloidal eyedrop gel 10.

In some embodiments, since the solution is a hydrophilic environment, and gatherings between hydrophilic ends and between the hydrophobic ends occurs to the amphipathic CHC molecules, the outer surface of the resulting CHC micelle 110 is a hydrophilic layer 111, and the interior is a hydrophobic layer 112. It is noted that though FIG. 1 only illustrates an outer layer of hydrophilic layer 111 and an inner layer of hydrophobic layer 112, in other embodiments, the CHC micelle 110 can include a plurality of alternating aligned hydrophilic layers 111 and hydrophobic layers 112 (unillustrated). Thus, in some embodiments, water-soluble drugs and lipid-soluble drugs can both be encapsulated in the CHC micelles 110.

In some embodiments, the compound prescription colloidal eyedrop gel 10 includes a first drug 130 inside the CHC micelle 110 and a second drug outside the CHC micelle 110. Both the first drug 130 and the second drug 140 have concentrations of about 0.01-50 mg/ml in the compound prescription colloidal eyedrop gel 10.

In terms of the category of drugs, the first drug 130 and the second drug 140 includes the glaucoma-treating drugs, such as the carbonic anhydrase inhibitors, the prostaglandin analogues and the beta blockers. The carbonic anhydrase inhibitors include but are not limited to acetazolamide, methazolamide, ethoxzolamide, dorzolamide, brinzolamide and dichlorphenamide; the prostaglandin analogues include but are not limited to latanoprost, travoprost, bimatoprost, tafluprosttrade and unoprostone; the beta blockers include but are not limited to timolol, befunolo, betaxolol, carteolol, levobunolol and betaophtiole.

Nonetheless, since drugs of the same category usually cause the problems of toxicity and cumulative side effects, the first drug 130 and the second drug 140 are not drugs of the same category, such as the combination of dorzolamide and brinzolamide which both belong to the carbonic anhydrase inhibitors. In some embodiments, the first drug 130 and the second drug 140 are selected from the group consisting of carbonic anhydrase inhibitors, prostaglandin analogues, and beta blockers, and the first drug 130 is different from the second drug 140. In some embodiments, the first drug 130 and the second drug 140 are respectively dorzolamide and latanoprost, brinzolamide and timolol, dorzolamide and timolol, latanoprost and timolol, latanoprost and dorzolamide, timolol and brinzolamide, timolol and dorzolamide, or timolol and latanoprost.

In terms of the hydrophobicity/hydrophilicity of drugs, in some embodiments, one of the first drug 130 and the second drug 140 is a water-soluble drug, and the other is a lipid-soluble drug. In some other embodiments, the first drug 130 and the second drug 140 are both water-soluble or lipid-soluble.

In addition, in order to maintain the solubility of the first drug 130, the second drug 140, and the CHC micelle 110 in the compound prescription colloidal eyedrop gel 10, a solvent (unillustrated) is included in the compound prescription colloidal eyedrop gel 10, and the concentration of the solvent is about 0.001-20% (w/v) relative to the compound prescription colloidal eyedrop gel 10. In some embodiments, the solvent is water, or both water and an organic solvent, the organic solvent is DMSO, ethanol, glycol, glycerol or a combination thereof. In some embodiments, the concentration of glycerol relative to the compound prescription colloidal eyedrop gel 10 is 5-20% (w/v). In another embodiment, the concentration of DMSO relative to the compound prescription colloidal eyedrop gel 10 is 0.001-0.1% (w/v). Due to differed polarities among the organic solvents, when the organic solvent is blended with water in different ratios, the polarity of the colloidal gel 10 can be adjusted, which selectively increase the solubility of the water-soluble drug or lipid-soluble drug in the colloidal gel 10, enabling both the water-soluble drug or the lipid-soluble drug to be disposed in the colloidal gel outside the CHC micelle 110.

In addition, with an aim to enhance the colloidal gel 10 to be well preserved and antiseptic, and to elongate the shelf life of the drug 130 and 140 in the colloidal gel 10, a preservative 150 is also included in the compound prescription colloidal eyedrop gel 10. In some embodiments, the preservative 150 has a concentration of about 0.001-0.01% (w/v) relative to the compound prescription colloidal eyedrop gel. In some embodiments, the preservative 150 includes benzalkonium chloride (BAK), chlorobutanol, phenylmercuric nitrate or a combination thereof. The benzalkonium chloride (BAK) belongs to an amine salt preservative. Although without high sterilizing and antiseptic level, it exhibits lower toxicity, irritation, and price, making it suitable for the compound prescription colloidal eyedrop gel 10 with long retention time on the eye. In some embodiments, the concentration of BAK in the compound prescription colloidal eyedrop gel 10 is 0.001-0.01% (w/v), which is decreased by 50%-95% compared to the BAK concentration of 0.02% (w/v) in an ordinary eyedrop. In some embodiments, the concentration of the preservative 150 is below 0.01% (w/v) to prevent harms caused by the preservative 150 to the eye (such as causing xerophthalmia) while still retains its preserving and antiseptic effect.

Moreover, in some embodiments, it is hard for the CHC micelles 110 to aggregate into the colloidal gel 10 due to the positive charges on the micelle surface. Thus, so as to facilitate the connection and aggregation among the CHC micelles 110, a negatively charged basic structural stabilizer 120 is further included in the compound prescription colloidal eyedrop gel 10 to make the surface of the CHC micelles 110 electrically neutral and facilitate the plurality of CHC micelles 110 to connect to one another and form the colloidal gel 10. In some embodiments, the basic structure stabilizer 120 has a concentration of 0.1-10% (w/v) in the compound prescription colloidal eyedrop gel 10, and the basic structure stabilizer 120 is genipin, sodium β-glycerophosphate, sodium hydroxide (NaOH), alginate, sodium bicarbonate ($NaHCO_3$), any suitable substance with negative charges and a combination thereof.

In some embodiments, through disposing the first drug 130 inside the micelle and the second drug 140 outside the micelle in the compound prescription colloidal eyedrop gel 10, the release rates of the first drug 130 and the second drug 140 can be modulated. In some embodiments, whether the drug is inside or outside the CHC micelle 110 depends on distinctions in the order of adding drugs in the method of making the compound prescription colloidal eyedrop gel 10.

Figure 2:
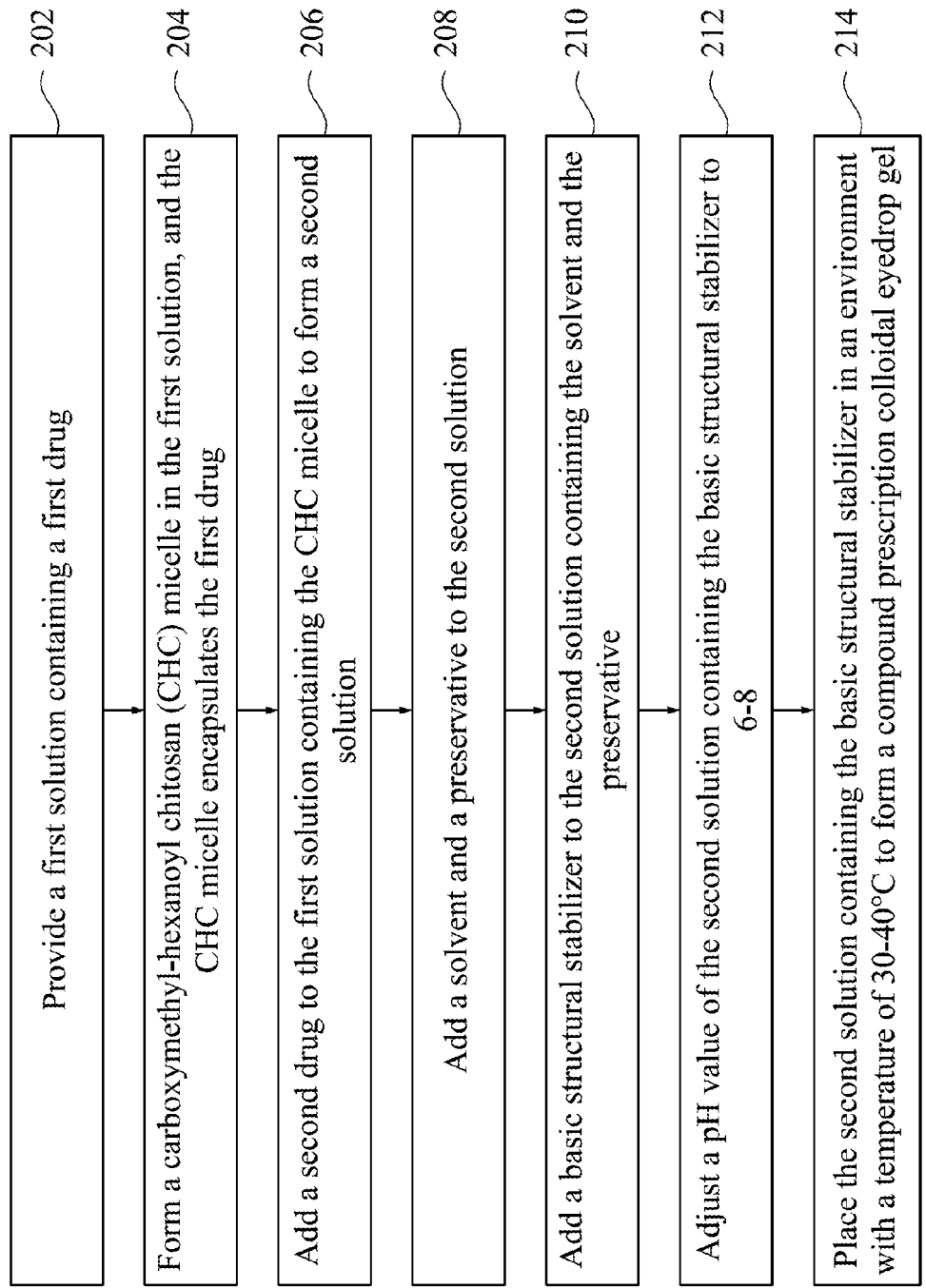
FIG. 2 illustrates a flow chart of making a compound prescription colloidal eyedrop gel in accordance with some embodiments of the present disclosure.

Referring to FIG. 2, which illustrates a flow chart of making a compound prescription colloidal eyedrop gel in accordance with some embodiments of the present disclosure. In step 202, making the compound prescription colloidal eyedrop gel 10 includes providing a first solution, and the first solution contains a first drug 130.

And then, in step 204, forming CHC micelles 110 in the first solution is performed. In some embodiments, forming the CHC micelles 110 in the first solution includes adding amphipathic CHC powder to the first solution. Since the first drug 130 has already been dissolved in the first solution before the amphipathic CHC powder dissolves and forms CHC micelles 110, the resulting CHC micelle 110 encapsulate the first drug 130.

In step 206, a second drug 140 is added to the first solution containing the CHC micelles 110 to form a second solution. Since the second drug is added after the formation of the CHC micelle 110, the second drug is not encapsulated in the CHC micelle 110.

In step 208, a solvent and a preservative 150 are added to the second solution.

In step 210, a basic structure stabilizer 120 is added to the second solution containing the solvent and the preservative 150 to connect the plurality of CHC micelles 110.

In step 212, a pH of the second solution containing the basic structure stabilizer 120 is adjusted to 6-8, more preferably adjusted to the pH of 6.6-7.8 that comforts human eyes, which at the same time encompasses the pH of human tears at 7.45±0.16 to reduce irritation and resulting tear secretions, thus reducing the loss of drugs. The adjustment of the pH is achieved by the titration of bases like the sodium hydroxide or acids like the hydrochloric acid into the second solution, to respectively elevate or lower the pH.

In step 214, the second solution containing the basic structure stabilizer 120 with adjusted pH is placed in an environment with a temperature of 30-40° C. for 20-40 minutes to make the fluid second solution to gradually solidify into the ointment-like form, honey-like form, or jelly-like form of compound prescription colloidal eyedrop gel 10.

EXAMPLES

The following examples are meant to elaborate the specific embodiments of the present disclosure in details to facilitate those skilled in the art to implement the present disclosure. The following examples are not meant to limit the present disclosure.

Comparative Examples 1-3

Thermostability Study of Colloidal Gels

Comparative examples 1-3 were prescription colloidal gels with the amphipathic CHC concentration of 1.2%, 1.8%, and 2.4% (w/v) respectively, each of which were further divided into 3 groups respectively placed in an environment with a temperature of 4° C., 25° C., and 37° C. to observe their morphology changes within 9 days. In the environment with the temperature of 4° C. and 25° C., Comparative examples 1-3 showed neither significant morphology change nor water yielding over the 9 days. However, in the environment with the temperature of 37° C., Comparative examples 1-3 all turned yellow and yielded water slightly. On account of this, regardless of level of the amphipathic CHC concentrations, prescription colloidal gel kept below room temperature (25° C.) exhibits fine stability.

Comparative Examples 2-4

Effect of Colloidal Gel Concentrations on the Drug Release

Besides examining the thermostability of the prescription colloidal gel, the drug release behavior of prescription colloidal gels in animals is a key factor of the effect of the prescription colloidal gels. The examining method of in vitro drug release included loading 0.5 mL of a prescription colloidal gel into a dialysis membrane, which was placed in a 1.5 mL centrifuge tube. The centrifuge tube was loaded with 1 ml of phosphate-buffered saline (PBS, pH 7.4), which simulated human body fluid and was renewed at predetermined time points, and the replaced PBS containing drugs was quantitatively analyzed by the high performance liquid chromatography (HPLC) to assess the amount of drugs released from the colloidal gels to dialyze across the dialysis membrane to the PBS.

Figure 3:
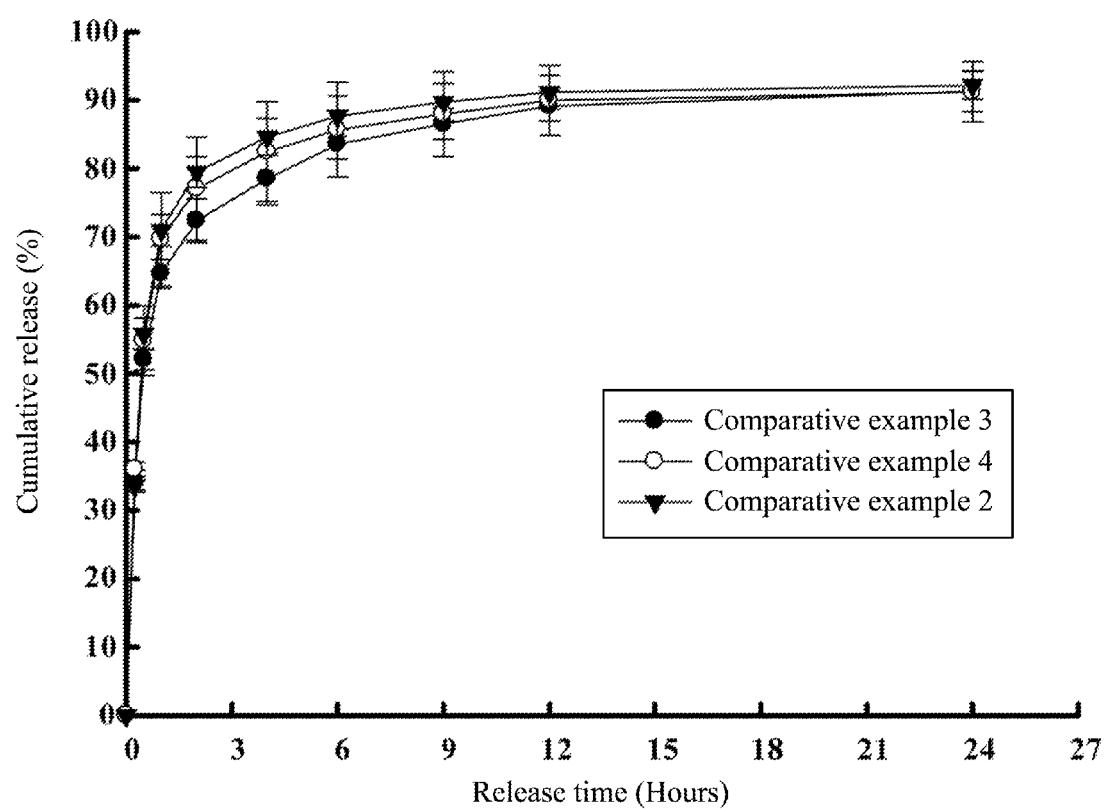
FIG. 3 illustrates a diagram of releases of drugs from prescription colloidal gels with different CHC concentrations against time in accordance with some comparative examples of the present disclosure.

Referring to FIG. 3, in which Comparative examples 2-4 were utilized to assess drug release rates of single prescription colloidal gels with different amphipathic CHC concentrations. Comparative example 4 was a prescription colloidal gel with the amphipathic CHC concentration of 2.1% (w/v), while Comparative examples 2-4 all included 20 mg/mL of the water-soluble drug dorzolamide. As shown in FIG. 3, the drug release rate of Comparative example 2 was the fastest, while the drug release rate of Comparative example 3 was the slowest. It manifests that with the increase in the content of amphipathic CHC, the viscosity and structural strength of the prescription colloidal gel also increase, which slows the drug release rates.

Comparative Examples 5-6

Effect of Drugs Inside or Outside CHC Micelles on the Drug Release

Figure 4A:
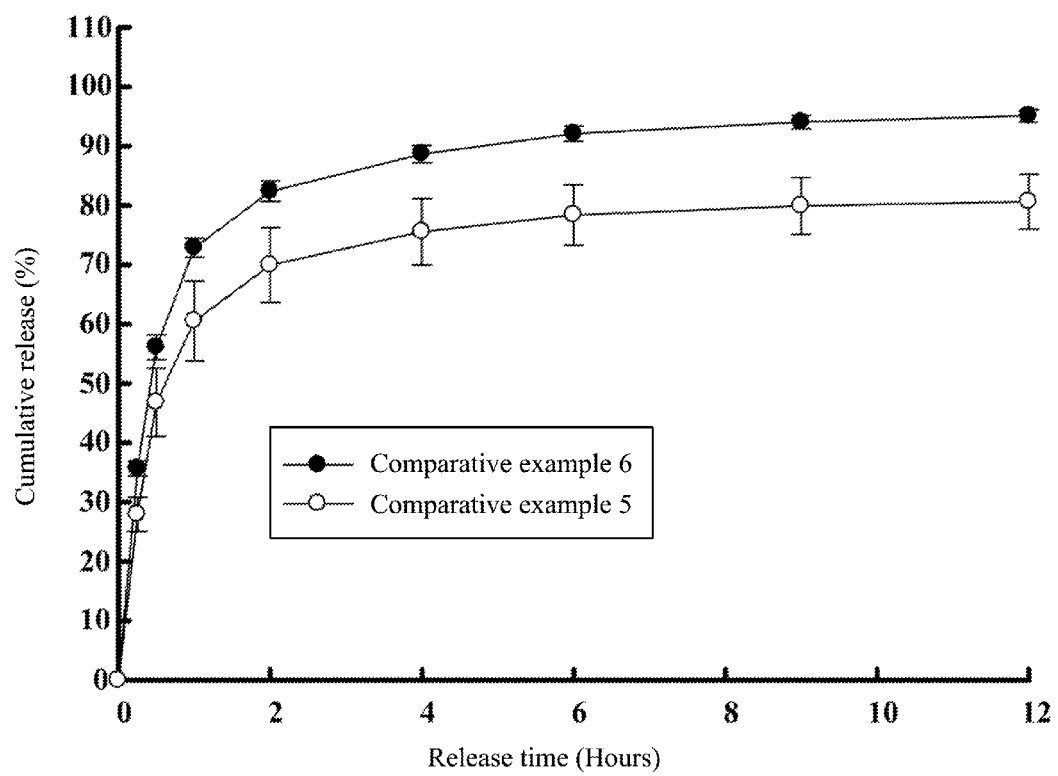
FIG. 4A-4B illustrate diagrams of releases of drugs respectively inside and outside CHC micelles against time in accordance with some comparative examples of the present disclosure.
Figure 4B:
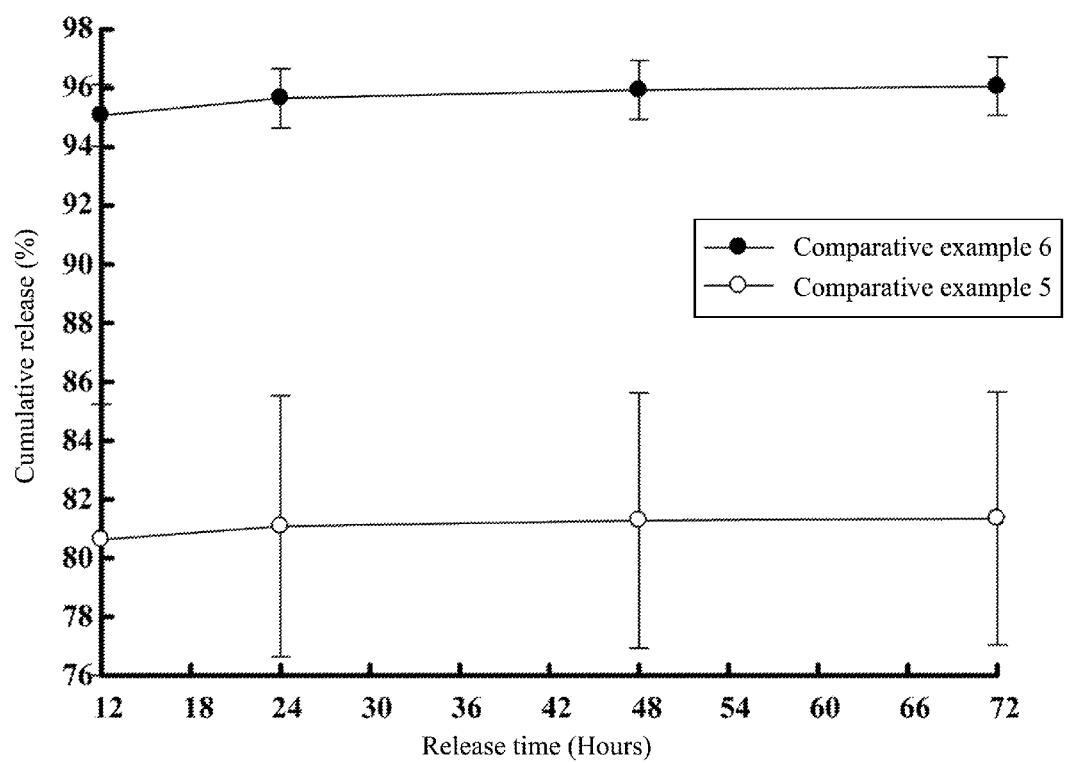

Please refer to FIG. 4A-4B, in which single prescription colloidal gels (Comparative examples 5-6) were utilized to assess the release of drugs inside or outside CHC micelles. Comparative example 5 was a prescription colloidal gel with the water-soluble drug dorzolamide inside the micelles and the amphipathic CHC concentration of 2.4% (w/v), while Comparative example 6 was a prescription colloidal gel with the water-soluble drug dorzolamide outside the micelles and the amphipathic CHC concentration of 2.4% (w/v). As shown in FIG. 4A, in the first 12 hours, the release rate of Comparative example 6 was faster than that of Comparative example 5, with the gap between release rates above 10% at the $2^{nd}$ hour. While at the $12^{th}$ hour, the release rate of Comparative example 5 was about 80%, while the release rate of Comparative example 6 already reached about 95%, with a gap between the two reaching 15%. Next, referring to FIG. 4B, during the 12-72 hours, the cumulative drug release rates of Comparative example 5 and Comparative example 6 were saturated with only slight increases, which were 81% and 96% respectively at the $72^{th}$ hour.

According to the above, drugs outside CHC micelles has a faster release rate. The drug release in Comparative example 5 was slower because the drug needed to break through the wall of the micelle, and then break through the colloidal gel body to be released, while the drug in Comparative example 6 only needed to break through the colloidal gel body to be released to the exterior. Thus, the drug release rate of Comparative example 5 was slower than that of Comparative example 6.

Experimental Example 1

Drug release of Compound Prescription Colloidal Gels

Figure 5:
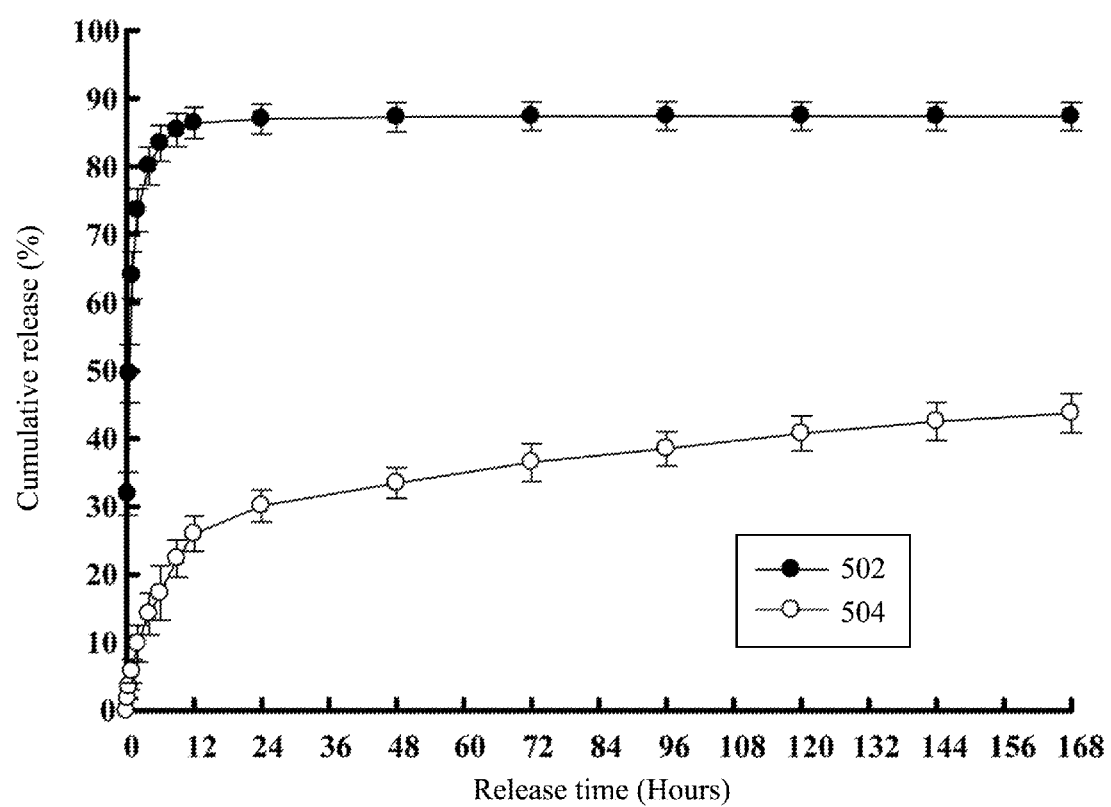
FIG. 5 illustrates a diagram of releases of compound prescription drugs respectively inside and outside CHC micelles against time in accordance with an experimental example of the present disclosure.

After realizing the release rate difference between single prescription drugs inside micelles and outside micelles, the study further investigated release rates of compound prescription drugs in colloidal gels, especially aimed at the study of release rate differences between water-soluble and lipid-soluble drugs inside or outside micelles. Referring to FIG. 5, which illustrates releases of compound prescription drugs respectively inside and outside CHC micelles against time in accordance with an experimental example of the present disclosure. Experimental example 1 was a compound prescription colloidal gel including both 20 mg/mL of water-soluble drug dorzolamide and 50 μg/mL of lipid-soluble drug latanoprost. In Experimental example 1, the first drug inside the CHC micelle was the water-soluble drug dorzolamide, while the second drug outside the CHC micelle was the lipid-soluble drug latanoprost.

As shown in FIG. 5, the cumulative release curve of the first drug (dorzolamide) is Line 502, while the cumulative release curve of the second drug (latanoprost) is Line 504. The drug of Line 502 was released rapidly, with the release rate of 85% at the $12^{th}$ hours; while the drug of Line 504 was released slowly, with the release rate of only 25% at the $12^{th}$ hours, and a gap between the two reached 60%. Nonetheless, from the $12^{th}$ hour, the cumulative release rate of Line 502 reached saturation, and the cumulative release rate was maintained at about 88% till the $168^{th}$ hour (the $7^{th}$ day). However, Line 504 showed constant and stable release, from the release rate of 20% at the $12^{th}$ hour to the release rate of 45% at the $168^{th}$ hour (the $7^{th}$ day), which indicated constant release of 25% throughout the subsequent 6.5 days, reaching over 2 folds of the cumulative release rates in the first 12 hours.

The release rate difference between the first drug (dorzolamide) and the second drug (latanoprost) arose from that the lipid-soluble latanoprost was disposed outside the CHC micelle, while the colloidal gel body between the outer layers of the CHC micelles was a hydrophilic environment, and thus it was difficult for the latanoprost to break through the hydrophilic environment and be released. In contrast to this, the water-soluble dorzolamide was inside the hrdrophilic region inside the CHC micelle. Despite the necessity to break through the micelle wall, once entry into the hydrophilic colloidal gel environment outside the micelle, the dorzolamide could rapidly diffuse and be released. Thus, even though the water-soluble drug was inside the micelle, it had a faster release rate than the lipid-soluble drug outside the micelle.

Based on the above Experimental example 1, adopting a water-soluble drug as the first drug inside the micelle can alleviate the rapid release of the water-soluble drug in the early stage, while adopting a lipid-soluble drug as the second drug outside the micelle can accelerate the release rate of the lipid-soluble drug, which reduces the gap of release rates between the first drug and the second drug, facilitating continuous and stable doses of drug release from the prescription colloidal gel both in the early stage and the late stage.

In addition, it is noted that Comparative example 5 in FIG. 4A-4B was the single prescription colloidal gel with the dorzolamide inside the CHC micelle, while Experimental example 1 in FIG. 5 was the compound prescription colloidal gel with the dorzolamide inside the CHC micelle. Although the dorzolamide of Comparative example 5 and Experimental example 1 were both inside the CHC micelle, the release rates of dorzolamide were different. The cumulative release rate of dorzolamide of Comparative example 5 was maintained at about 81% in 12-72 hours, while the cumulative release rate of dorzolamide of Experimental example 5 reached about 88% in 12-72 hours. This indicates that in the compound prescription colloidal gel with the first drug inside the micelle and the second drug outside the micelle, the release rates of the individual drugs in the compound prescription colloidal gel are not the same as in the single prescription colloidal gel. Since that the first drug and the second drug are respectively inside and outside the micelle, and that the two drugs affect each other in the colloidal gel during the release, alterations in drug release rates are generated, which facilitates more effective tuning of drug release rates.

In some embodiments, a lipid-soluble drug inside the micelle is disposed in the hydrophobic layer of the micelle, and thus would need to break through the micelle wall and the hydrophilic colloidal gel outside the micelle to be released, rendering its release rate slower than the lipid-soluble drug outside the micelle. Relatively, in some embodiments, a water-soluble drug outside the micelle is already in the hydrophilic colloidal gel environment, and can thus diffuse and be released at the most fastest rate, which is faster than the release rate of the water-soluble drug inside the micelle. According to this, in some embodiments, drug release rates from the fastest to the slowest are sequentially: the water-soluble drug outside the micelle, water-soluble drug inside the micelle, lipid-soluble drug outside the micelle, and the lipid-soluble drug inside the micelle.

Thus, in some embodiments, when the first drug is a lipid-soluble drug and the second drug is a water-soluble drug, the release rate of the first drug is slow, while the release rate of the second drug is very rapid, and a gap between the two release rates is huge. In some embodiments, when the first drug is a water-soluble drug and the second drug is a lipid-soluble drug, the release rate of the first drug is faster, while the release rate of the second drug is slower. In some embodiments, when the first drug and the second drug are both water-soluble drugs, the first drug is released rapidly, while the release rate of the second drug is even more rapid. In some embodiments, when the first drug and the second drug are both lipid-soluble drugs, the second drug is released slowly, while the release rate of the first drug is even slower.

According to the above, the present disclosure provides a compound prescription colloidal eyedrop gel. By disposing the first drug inside the CHC micelle while the second drug outside the CHC micelle, changes to the drug release rates can be induced, which further facilitates coupling of the drug release rates to cater to patients' needs for different eyedrop dropping frequencies. For instance, by disposing the water-soluble drug inside the micelle, the burst release of the water-soluble drug in the early stage can be alleviated, while still providing rapid, immediate treatment. By disposing the lipid-soluble drug outside the micelle, the slow release of the lipid-soluble drug in the late stage can be accelerated to compensate for the substantially reduced release amount of the water-soluble drug in the late stage, facilitating the proceeding of the subsequent treatment. By applying the two different kinds of drugs with different release rates onto the eye at once, the aqueous humor can be dredged and the ocular pressure can be lowered, achieving the constant and progressive treatment and lowering the dropping frequency of the prescription colloidal gel.

In addition, although the abovementioned compound prescription colloidal eyedrop gel includes only two kinds of drugs, a compound prescription colloidal gel including three or more kinds of drugs can also apply the method of making of the compound prescription colloidal eyedrop gel of the present disclosure to facilitate at least one of the three or more drugs to be disposed inside the CHC micelle without departing from the spirit of the present disclosure. For instance, by providing a first solution containing a first drug and a second drug, adding amphipathic CHC powder into the first solution to form a CHC micelle, adding a third drug into the first solution containing the CHC micelle, and then adding a solvent, a preservative, and a basic structure stabilizer, the formation of a compound prescription gel with the first drug and the second drug inside the CHC micelle and the third drug outside the CHC micelle can be achieved.

Despite the embodiments disclosed above, these are not meant to limit the present disclosure. It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A compound prescription colloidal eyedrop gel, comprising:
a plurality of carboxymethyl-hexanoyl chitosan (CHC) micelles, wherein each of the CHC micelles has an inner hydrophobic layer and an outer hydrophilic layer;
a basic structural stabilizer connecting the plurality of CHC micelles;
a first drug inside the CHC micelle, wherein the first drug is a water-soluble drug; and
a second drug outside the CHC micelle, wherein the second drug is a lipid-soluble drug.

2. The compound prescription colloidal eyedrop gel of claim 1, wherein the first drug and the second drug are selected from the group consisting of carbonic anhydrase inhibitors, prostaglandin analogues for the treatment of glaucoma, and beta blockers; and the first drug is different from the second drug.

3. The compound prescription colloidal eyedrop gel of claim 1, wherein both the first drug and the second drug have concentrations of about 0.01-50 mg/ml in the compound prescription colloidal eyedrop gel.

4. The compound prescription colloidal eyedrop gel of claim 1, wherein the plurality of CHC micelles has a concentration of about 0.1-5% (w/v) in the compound prescription colloidal eyedrop gel.

5. The compound prescription colloidal eyedrop gel of claim 1, further comprising a solvent, and the solvent is water, or both water and an organic solvent, and the organic solvent is glycerol, DMSO, ethanol, glycol or a combination thereof, and the solvent has a concentration of about 0.001-20% (w/v) relative to the compound prescription colloidal eyedrop gel.

6. The compound prescription colloidal eyedrop gel of claim 1, further comprising a preservative, and the preservative is benzalkonium chloride (BAK), chlorobutanol, phenylmercuric nitrate or a combination thereof, and the preservative has a concentration of about 0.001-0.01% (w/v) relative to the compound prescription colloidal eyedrop gel.

7. The compound prescription colloidal eyedrop gel of claim 1, wherein the basic structural stabilizer is genipin, sodium β-glycerophosphate, sodium hydroxide, alginate or a combination thereof, and the basic structural stabilizer has a concentration of about 0.1-10% (w/v) in the compound prescription colloidal eyedrop gel.

8. A method of making a compound prescription colloidal eyedrop gel of claim 1, the method comprising:
   providing a first solution comprising the first drug;
   forming a carboxymethyl-hexanoyl chitosan (CHC) micelle in the first solution, wherein the CHC micelle encapsulates the first drug;
   adding the second drug to the first solution comprising the CHC micelle to form a second solution;
   adding the basic structural stabilizer to the second solution; and
   placing the second solution comprising the basic structural stabilizer in an environment with a temperature of 30-40° C. to form the compound prescription colloidal eyedrop gel.

9. The method of claim 8, wherein forming the carboxymethyl-hexanoyl chitosan (CHC) micelle in the first solution comprises adding amphipathic carboxymethyl-hexanoyl chitosan (CHC) powder to the first solution.

10. The method of claim 8, further comprising adding a solvent and a preservative to the second solution before adding the basic structural stabilizer to the second solution.

11. The method of claim 8, further comprising adjusting a pH value of the second solution comprising the basic structural stabilizer to a pH of 6-8 after adding the basic structural stabilizer to the second solution.

* * * * *